United States Patent
O'Neill (10) Patent No.: US 10,271,736 B2
(45) Date of Patent: Apr. 30, 2019

(54) LOW COST MAGNETIC RESONANCE SAFE PROBE FOR TEMPERATURE MEASUREMENT

(71) Applicant: KONINKLIJKE PHILIPS N.V., Eindhoven (NL)

(72) Inventor: Francis Patrick O'Neill, Kissimee, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 401 days.

(21) Appl. No.: 15/302,529

(22) PCT Filed: Mar. 31, 2015

(86) PCT No.: PCT/IB2015/052351
§ 371 (c)(1),
(2) Date: Oct. 7, 2016

(87) PCT Pub. No.: WO2015/159171
PCT Pub. Date: Oct. 22, 2015

(65) Prior Publication Data
US 2017/0027449 A1 Feb. 2, 2017

Related U.S. Application Data

(60) Provisional application No. 61/979,539, filed on Apr. 15, 2014.

(51) Int. Cl.
*G01V 3/00* (2006.01)
*A61B 5/01* (2006.01)
(Continued)

(52) U.S. Cl.
CPC .............. *A61B 5/01* (2013.01); *A61B 5/0008* (2013.01); *A61B 5/055* (2013.01); *G01K 7/24* (2013.01);
(Continued)

(58) Field of Classification Search
CPC ....................................................... A61B 5/01
(Continued)

(56) References Cited

U.S. PATENT DOCUMENTS 4,531,842 A 7/1985 Schonberger
5,653,239 A 8/1997 Pompei
(Continued)

FOREIGN PATENT DOCUMENTS

EP 0213239 3/1987
EP 0498996 8/1992
(Continued)

OTHER PUBLICATIONS

Hofman, et al., "Transeophageal Cardiac Pacing During Magnetic Resonance Imaging: Feasibility and Safety Considerations", Magnetic Resonance in Medicine, vol. 35. No. 3, Mar. 1, 1996.
(Continued)

*Primary Examiner* — Louis M Arana (57) ABSTRACT

A temperature measurement probe (130) for use in a magnetic resonance environment, includes an elongated substrate (202), at least one highly resistive, electrically conductive traces (200, 200a, 200b, 200a', 200b') one printed at least one thermistor (204) disposed on the substrate and electrically connected with the trace. The thermistor is configured to be placed in thermal communication with a patient in the magnetic resonance environment. In some embodiments, the printed trace may be carbon-based, silicone based, or may be a doped semiconductor material.

15 Claims, 5 Drawing Sheets

(51) Int. Cl.
*A61B 5/00* (2006.01)
*A61B 5/055* (2006.01)
*G01R 33/28* (2006.01)
*G01R 33/31* (2006.01)
*G01K 7/24* (2006.01)

(52) U.S. Cl.
CPC .......... *G01R 33/288* (2013.01); *G01R 33/31* (2013.01); *A61B 2562/0271* (2013.01)

(58) Field of Classification Search
USPC ........................................ 324/314, 318, 322
See application file for complete search history.

(56) References Cited

U.S. PATENT DOCUMENTS

| | | |
|---|---|---|
| 5,730,134 A | 3/1998 | Dumoulin |
| 6,270,463 B1 | 8/2001 | Morris |
| 8,801,272 B2 | 8/2014 | Bieberich |
| 2006/0241392 A1 | 10/2006 | Feinstein |
| 2006/0247509 A1 | 11/2006 | Tuccillo |
| 2010/0219085 A1* | 9/2010 | Oviatt, Jr. .......... A61B 5/14532 205/782 |
| 2010/0244833 A1 | 9/2010 | Sakakura |
| 2011/0249699 A1 | 10/2011 | Bieberich |
| 2015/0141792 A1 | 5/2015 | O'Neill |
| 2018/0064348 A1* | 3/2018 | Tsuchimoto ............. A61B 5/01 |
| 2018/0206729 A1* | 7/2018 | Wang ...................... A61B 5/01 |

FOREIGN PATENT DOCUMENTS

| | | |
|---|---|---|
| JP | 6249716 | 9/1994 |
| JP | 2004-219098 | 8/2004 |
| WO | 2013175457 | 11/2013 |

OTHER PUBLICATIONS

Weiss, et al., "Evaluation of a novel MR-RF ablation catheter with full clinical functionality", Proceedings of the International Society for Magnetic Resonance in Medicine, May 2011.

* cited by examiner

LOW COST MAGNETIC RESONANCE SAFE PROBE FOR TEMPERATURE MEASUREMENT

CROSS REFERENCE TO RELATED APPLICATIONS

This application is the U.S. National Phase application under 35 U.S.C. § 371 of International Application No. PCT/IB2015/052351, filed Mar. 31, 2015, published as WO 2015/159171 on Oct. 22, 2015, which claims the benefit of U.S. Provisional Patent Application No. 61/979,539 filed Apr. 15, 2014. These applications are hereby incorporated by reference herein.

The following relates generally to a temperature monitoring apparatus and method that can operate in a magnetic resonance (MR) environment. It finds particular application in conjunction with low cost, high resistance non-magnetic printed traces, which operate near a magnetic resonance imaging scanner, and will be described with particular reference thereto. However, it will be understood that it also finds application in other usage scenarios and is not necessarily limited to the aforementioned application.

Temperature monitoring devices need to be used in MR environments to monitor the condition of the patient. Current accepted methods include the use of a fiber optic probe. A fiber optic cable is connected to the sensing element on the patient, and to the patient monitoring device. However, these fiber optic cables are expensive, can be mechanically delicate, and may suffer from errors as a result of atomic level changes in the sensor material due to strong magnetic fields. The use of a standard thermistor in an MR environment would require the use of a distributed or discrete high-resistance cable to connect the sensor to the monitor to overcome the RF heating effects and burn hazards associated with the MR environment. These high resistance cables are expensive and do not fully eliminate the burn hazard to patients. In addition, these cables are difficult to manufacture, are susceptible to triboelectric effects, suffer from inductive pickup, excessive parasitic capacitance, and are hyper sensitive to patient movement. For example, ferromagnetic content used in the construction of the temperature-monitoring device may cause the cable to be drawn into the MRI scanner causing damage to the patients, users, or causing the equipment to act as a projectile. Additionally, the radio frequency field produced by the MRI scanner may generate currents in a standard cable using a standard thermistor, or cause "hot-spots" that may increase surface temperatures enough to exceed those allowed by regulatory standards and pose discomfort or a burn hazard to the patient. Further, the MRI gradient interference from the MR scanner can also induce currents on standard cables and thermistors and on the connection points producing an additive interference waveform component that potentially gives a false temperature reading.

The present application discloses a new and improved temperature-monitoring device for use in an MR environment, which addresses the above referred issues, and others.

According to one aspect, a temperature measurement probe for use in a magnetic resonance environment, is disclosed. The printed conductor includes an elongated substrate, at least one highly resistance, electrically conductive trace printed on the substrate, and at least one thermistor disposed on the substrate and electrically connected with the trace, the thermistors configured to be placed in thermal communication with a patient in the magnetic resonance environment.

According to another aspect, a magnetic resonance system is disclosed. The system includes a magnetic resonance scanner and a temperature measurement probe as set forth in the proceeding paragraphs, the temperature measurement probe being disposed in an examination region of the magnetic resonance scanner.

According to another aspect, a method for monitoring patient temperature readings during an MRI is disclosed. The method includes printing a highly resistive, electrically conductive trace on an elongated substrate and electrically connecting at least one thermistor disposed on the substrate with the trace.

Another advantage resides in the elimination of ferromagnetic content.

Another advantage resides in the reduction of patient burn risks.

Another advantage resides in ability to disinfect the thermistor probe.

Another advantage resides in improved patient care.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

Figure 1:
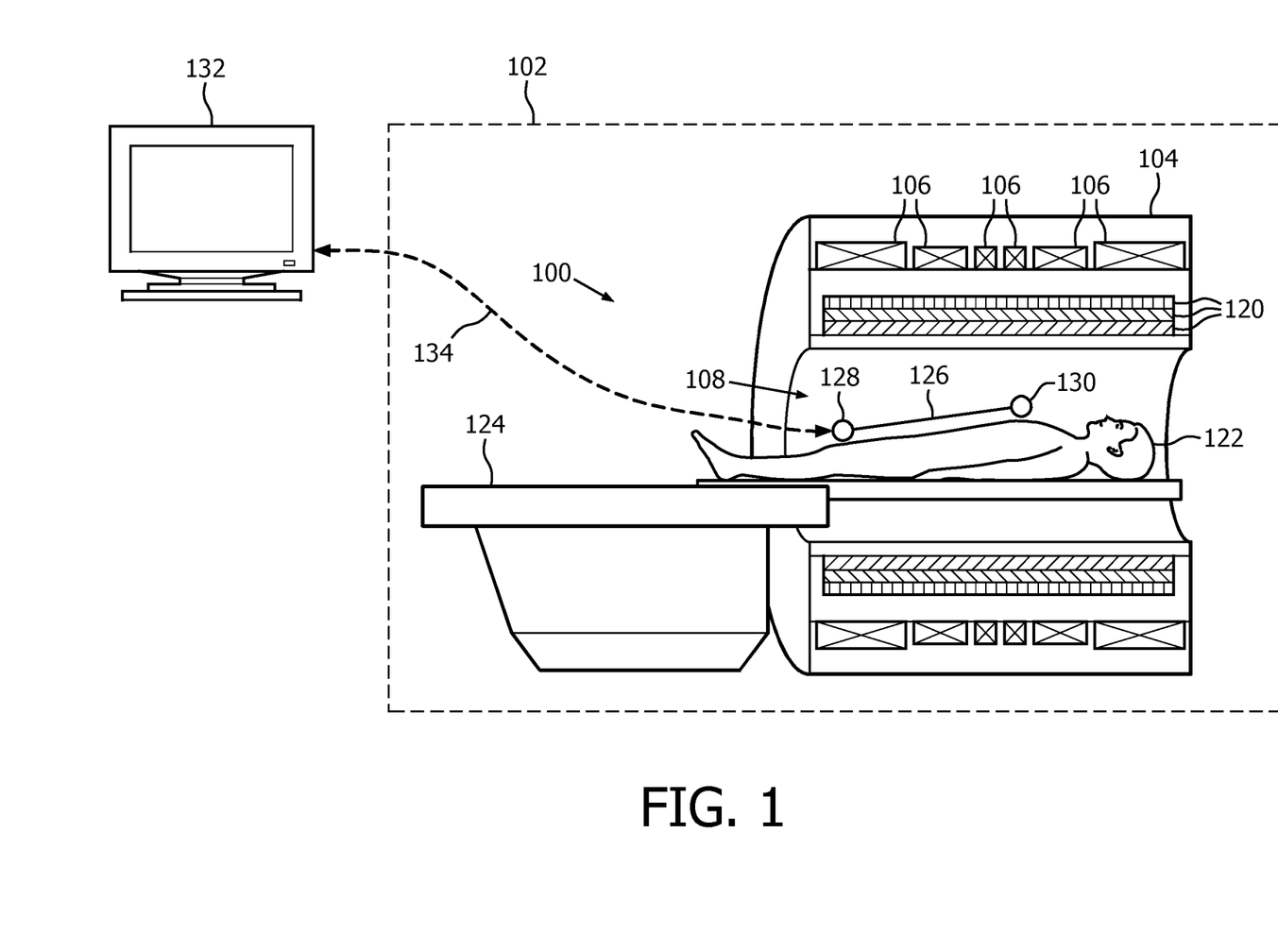
FIG. 1 diagrammatically shows a magnetic resonance (MR) system with a temperature monitoring apparatus operating inside the MR scanner.

With reference to FIG. 1, a magnetic resonance environment includes a magnetic resonance (MR) scanner 100 disposed in a radio frequency isolation room 102 (diagrammatically indicated by a dashed box surrounding the MR scanner 100). For example, a wire mesh or foil define a Faraday cage or other radio frequency screening structures embedded in or disposed on the walls, ceiling, and floor of the MR room containing the MR scanner 100. The MR scanner 100 is shown in diagrammatic side-sectional view in FIG. 1, and includes a housing 104 containing a main magnet windings 106 (typically superconducting and contained in suitable cryogenic containment, not shown, although a resistive magnet windings are also contemplated) that generate a static ($B_0$) magnetic field in a bore 108 or other examination region. The housing 104 also contains magnetic field gradient coils 120 for superimposing magnetic field gradients on the static ($B_0$) magnetic field. Such gradients have numerous applications as is known in the art, such as spatially encoding magnetic resonance, spoiling magnetic resonance, and so forth. An imaging subject, such as an illustrative patient 122, or an animal (for veterinary imaging applications), or so forth is loaded into the examination region (inside the bore 108 in the illustrative case) via a suitable couch 124 or other patient support/transport apparatus. The MR scanner may include numerous additional components known in the art, which are not shown for simplicity, such as magnetic field shims, a whole body radio frequency (RF) coil disposed in the housing 104, and so forth. The MR scanner also typically includes numerous auxiliary or ancillary components again not shown for simplicity, such as power supplies for the main magnet 106 and the magnetic field gradient coils 120, local RF coils (e.g. surface coils, a head coil or limb coil, or so forth), RF transmitter and RF reception hardware, and various control and image reconstruction systems, by way of some examples. Moreover, it is to be understood that the illustrative MR scanner 100, which is a horizontal bore type scanner, is merely an illustrative example and that more generally the disclosed MR safe cables and electrodes are suitably employed in conjunction with any type of MR scanner (e.g., a vertical bore scanner, open-bore scanner, or so forth).

In operation, the main magnet 106 operates to generate a static $B_0$ magnetic field in the examination region 108. RF pulses are generated by the RF system (including for example a transmitter and one or more RF coils disposed in the bore or a whole-body RF coil in the housing 104) at the Larmor frequency (i.e., magnetic resonance frequency) for the species to be excited (usually protons, although other species may be excited, e.g. in MR spectroscopy or multi-nuclear MR imaging applications). These pulses excite nuclear magnetic resonance (NMR) in the target species (e.g., protons) in the subject 122, which are detected by a suitable RF detection system (e.g., a magnetic resonance coil or coils and suitable receiver electronics). Magnetic field gradients are typically applied by the gradient coils 120 before or during excitation, during a delay period (e.g., time to echo or TE) period prior to readout, and/or during readout in order to spatially encode the NMR signals. An image reconstruction processor applies a suitable reconstruction algorithm comporting with the chosen spatial encoding in order to generate a magnetic resonance image, which may then be displayed, rendered, fused or contrasted with other MR images and/or images from other modalities, or otherwise utilized.

Figure 2A:
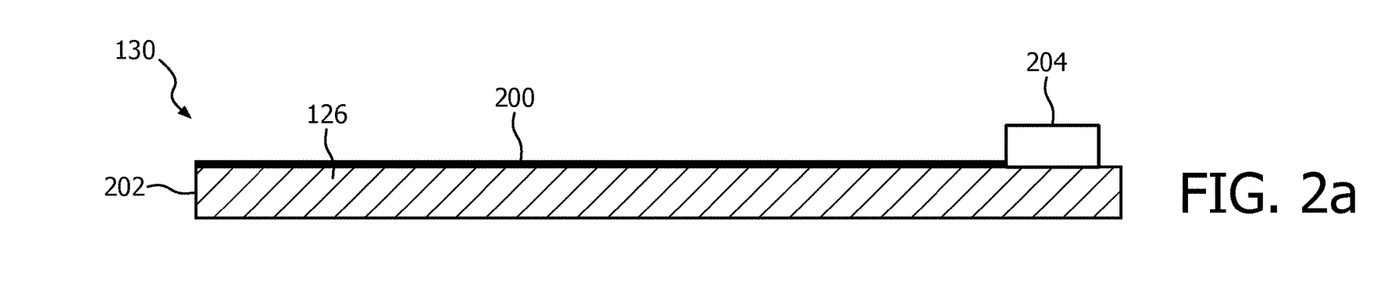
FIG. 2a is a cross-sectional view diagrammatically showing a substrate with a printed trace with applicable thermistors.
Figure 2B:
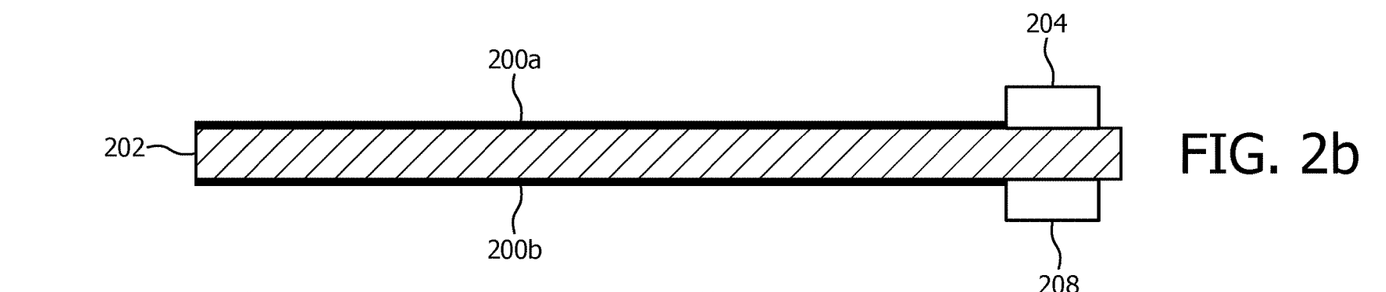
FIG. 2b is a side view in partial section diagrammatically showing a temperature sensing thermistor and a reference element on opposite faces of a substrate.
Figure 2C:
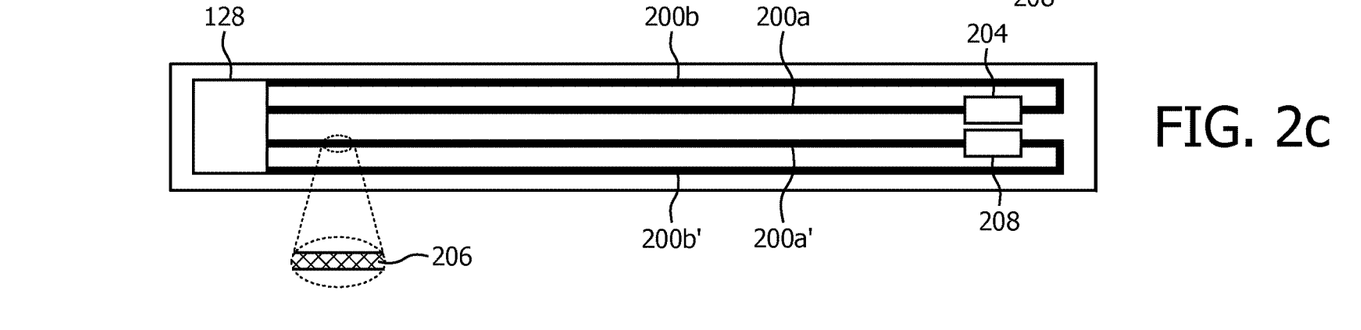
FIG. 2c is a top view diagrammatically showing two printed traces with a temperature sensing thermistor and reference element on a common surface of a substrate.

With continuing reference to FIG. 1 and further reference to FIGS. 2a-2c, as part of or ancillary to the MR procedure, temperature measurements are acquired using a temperature measurement probe 130. In illustrative FIG. 1, a printed conductor for temperature measurement probe 130 is displayed on the patient 122 and in connection with a monitor 132 (located outside or optionally inside) the MR chamber 102. The temperature-measurement probe 130 may have sufficiently low power consumption that the temperature function may be integrated into a battery powered control and processing circuit 128 that communicates wirelessly 134 (showing as a dashed line from the battery powered control and processing circuit to the monitor) with the monitor 132. The temperature measurement probe 130 with a conductive trace printed cable 126 and the battery powered control and processing circuit 128 may record surface or invasive temperature measurements of the patient 122. The conductive trace printed cable 126 may further be integrated into other cables particularly for surface use.

Further reference to FIGS. 2a-2c a controlled resistance printed electrical trace or conductive trace, 200 is printed on a flexible, MR neutral substrate 202 to form the planar lead cable 126 between a thermistor 204 on the patient 122 and the sensing monitor 128. The substrate 202 may be any flexible magnetic resonance inert planar material such as a polymer resin-based film or Mylar. The substrate 202 material is selected so that Proton emissions do not degrade the MR image. In various embodiments, the conductive trace 200 is formed of carbon-based ink. The conductive trace 200 may optionally be silicon based or may be made from a doped semiconductor material. Further, the printed conductive traces 200 and thermistors 204 should be non-ferromagnetic to inhibit distortion of magnetic fields and to inhibit the magnetic field and gradient from adversely affecting the probe.

With continuing reference to FIG. 2a-2c, the conductive trace 200 is configured to inhibit eddy current from forming in the trace and causing resistive heating. The traces can be of high resistance and can include slots or other constructs that inhibit eddy current loops. Connection probes are printed or applied at the thermistor end of the trace and a control and processing circuit to facilitate connection to the thermistor 204 and the control and processing circuit 128. In other embodiments, the conductive printed trace may be solid or may contain features such as cross-hatching to inhibit eddy current generation in the conductive printed trace. The cross-hatching 206 in the trace 204 improves functional performance by reducing the induction of interference currents in the electrode and resistive traces from the RF and gradient magnetic fields. By printing the conductive trace and the thermistor lead connections of the temperature probe 130, repeatability, and reproducibility of the lead-wire characteristics, routing is facilitated.

The thermistor 204 is a high resistance thermistor preferably on the order of 10,000 k Ohms, tuned to respond linearly in the range of human body temperatures with the low cost. The printed conductive trace 200 resistance can be in the order of 8-10 k Ohms per foot, which may be achieved by printing with a conductive ink in the order of 10 ohms per square. The printed conductive trace resistance can be laser trimmed to achieve a desired target resistance to narrow the traces or by forming eddy current inhibiting longitudinal slots. The thermistor 204 may be attached by surface mount leads or attached used conductive leads.

In the embodiment, illustrated in FIG. 2b-c, temperature sensitive thermistor 204 and a reference resistor or thermistor 208 are connected in loops with printed input and output traces 200a, 200b, which are printed on opposite faces of the substrate 202. One of the thermistors is applied to the patient and the reference element is thermally isolated from the patient or is selected to have stable resistance across the temperature range of interest. In this manner, the temperature sensing element signal is indicative of temperature with RF field induced currents to and the reference element signal is indicative of RF field induced currents which allow for elimination of RF field induced currents by using a common mode filter.

In other embodiments, the resistance may be evenly or unevenly distributed along the printed conductive cable trace 200. Uneven distribution can be achieved by varying the width and or thickness of the printing pattern. Notch or low pass filed integrated circuit components, antenna circuits, power supplies, sensors (piezo, MEMS, accelerometers) may be optionally incorporated into the printed conductive cable trace 200.

In another embodiment illustrated in FIG. 2c, a circuit is formed by the temperature sensing thermistor 204, and the reference elements 208, e.g. a reference resistor, two input traces 200a, 200b, two return traces 200b, 200b' connected to the two input traces 200a, 200b (connection not shown) disposed on a common face of the substrate 202 and the processing and control circuit 128.

Figure 2D:
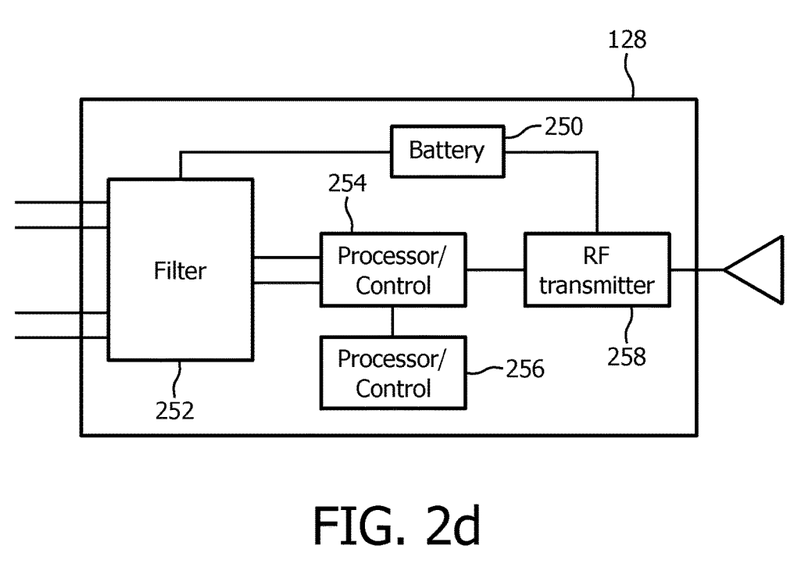
FIG. 2d is illustrative of a circuit for converting the thermistor output to temperature.

With reference to FIG. 2d, the resistance of a thermistor changes with temperature. The process and controlled circuit 128 translates the currents through or voltages across the thermistors into temperature values for transmission to the monitor 132. The circuit includes a battery 250 or other power supply outside of the MR environment. A filter 252 corrects for noise in the thermistor signals, e.g., by subtracting the noise signal from the reference element 200 from the noisy temperature signal from the temperature measuring thermistor 204. A control or processor 254 converts the temperature into a temperature, e.g. using a look-up table stored in an EPROM 256. The look-up table can further compensate for variations from one temperate sensor to the next. An RF transmitter 258 transmits the determined temperature value to an RF receiver connected with the monitor 132. It is to be appreciated that the filtering and the conversion to temperature can, in full or in part, be performed at the monitor 132.

In various embodiments, the printed conductive traces 200 are suitably formed of carbon-based ink with specific electrical resistance applied to the planar flexible substrate with predefined electrical resistance applied to the planar flexible substrate 202 to achieve the desired resistance and thermal characteristics. The printed conductive traces 200 may be applied by any reproductive method such as by screen-printing. The printed conductive traces 200 may be solid or may contain features such as hatching, longitudinal slots, or the like.

Figure 3:
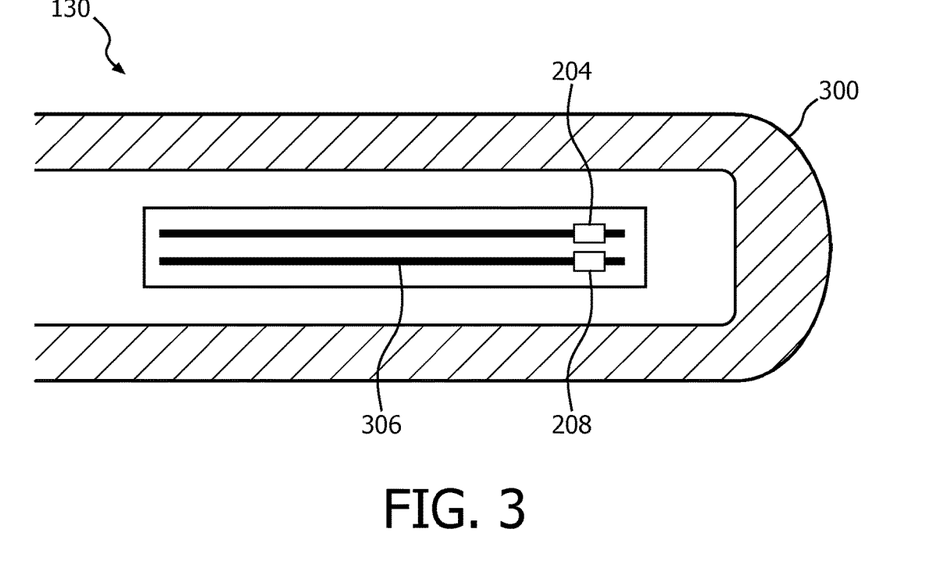
FIG. 3 diagrammatically shows a printed trace and thermistor temperature measurement device in a protective housing or catheter shown in section.

With reference to FIG. 3, a side sectional view of the temperature measurement probe is displayed. A protective jacket 300 covers the probe and can provide electrical insulation and protection. The protective layer 300 is preferably electrically insulating compared with the material of the printed conductive traces 200, and non-ferromagnetic and MR compatible. For one-time use probes the protective layer is ideally a material that is low cost and sterilisable. The sterilisiable protective jacket allows the probe to be inserted into the patient during an MR to provide internal temperature measurement to further protect from injury to the patient. The protective layer 300 can have a foam insulating layer to insulate the circuit from induction of interference currents in the electrode and resistive traces from static and gradient magnetic fields. Again, a reference resistor or thermistor 208 may be added to create the common mode signal for subtraction from the patient temperature measuring thermistor 204 to compensate for the common mode. The housing 300 can be part of a catheter that is configured for other functions.

Figure 4:
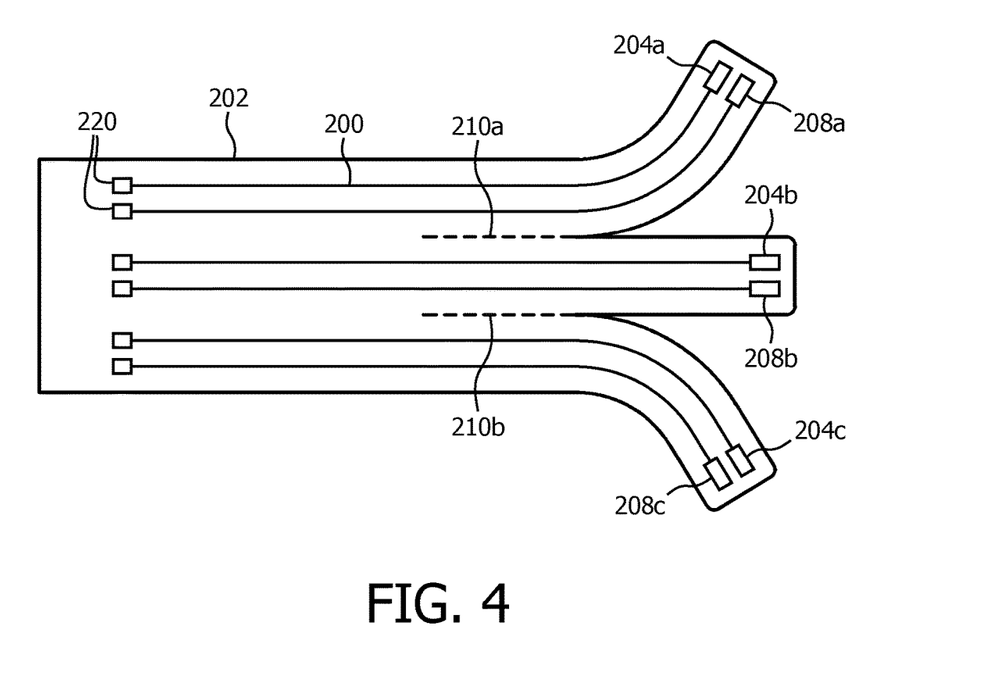
FIG. 4 diagrammatically shows a plurality of temperature sensors disposed on a common substrate with tear lines in the elongated substrate that enable placement of the sensors at a plurality of locations.

With reference to FIG. 4, the temperature measurement probe 130 may include a plurality of printed traces on one face of the elongated substrate 202, a plurality of return traces (not shown) on an opposite face, a plurality of thermistors 204a, 204b, 204c, and a plurality of reference elements 208a, 208b, 208c. In some embodiments, connection pads 220, e.g. silver chloride, are printed on the traces to facilitate connection to the thermistor, the reference element, and the circuit. Tear lines 210a, 210b, are defined in the elongated substrate 202. The tear lines 210a, 210b in the substrate 202 allow the printed traces 200a, 200b, 200c to be separable to accommodate multi-site sensing on various patient body types.

Figure 5:
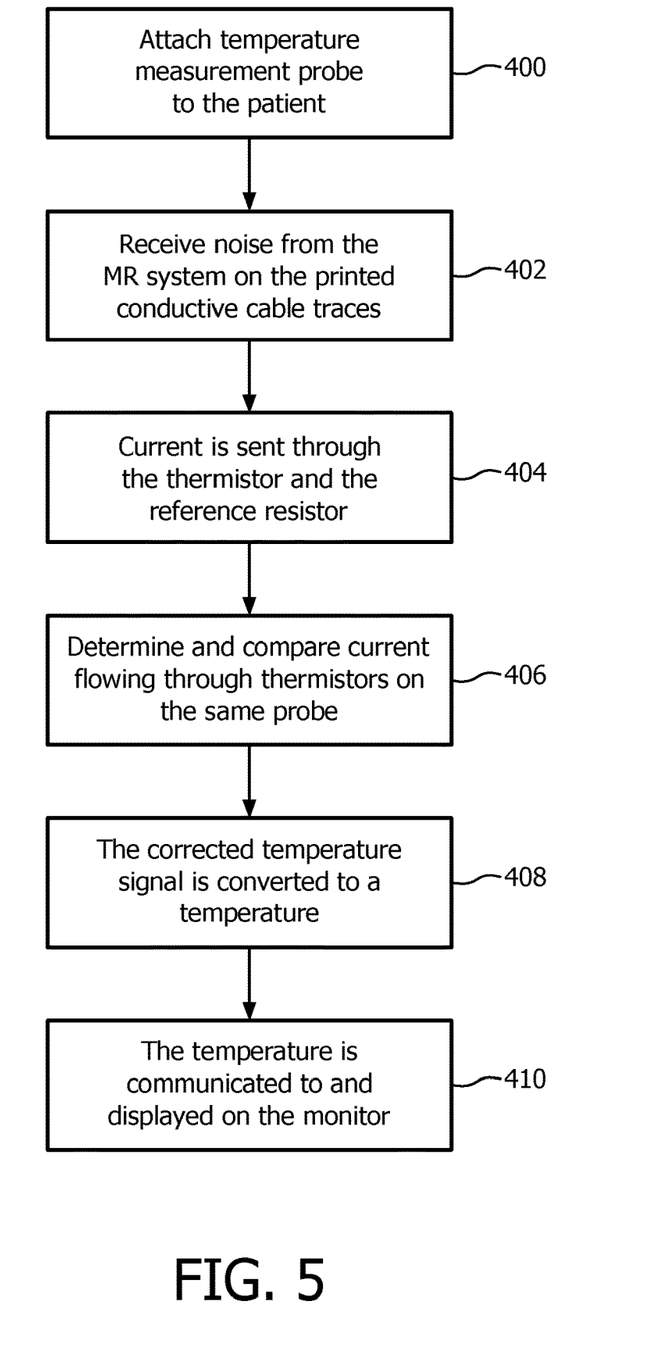
FIG. 5 illustrates a method for monitoring patient temperature readings during a MRI using the printed conductor disclosed herein.

With reference to FIG. 5, initially, the substrate is cut to size and the conductive traces and the connection pads are printed on the substrate. The thermistor 204, the reference element 208, and the circuit 128 are connected to the connection pads. To avoid burns or other injury to patient during an MR, the temperature of the probe is monitored during operation. In a step 400, the printed conductor for temperature measurement probe 130 is attached to the patient 122. The printed conductor 126 of temperature measurement probe 130 is connected to a patient monitor 132 either wirelessly 134 or through a wired connection. Upon activation of the MR system 100, in a step 402, the probe receives a noise on the printed trace 200 created by the MR system 100. The probe 130 preferably contains a reference element 208, e.g. a reference resistor or a reference thermistor. In a step 404, a current is sent through the thermistor 204 and the reference element 208. In a step 406, the currents flowing through the thermistor 204 and the reference element 208 are determined and compared. The current through the thermistor is indicative of the MR induced noise and temperature. The current through the reference resistor is indicative of MR induced noise. The comparison of the current flowing through the reference element 208 and the thermistor 204 allows the current or signal from the thermistor 204 to be corrected for noise. In a step 408, the corrected temperature signal is converted to a temperature, e.g. with a look-up table. In a step 410, the temperature is communicated to and displayed on the monitor 132, e.g. by RF transmission lines.

The invention has been described with reference to the preferred embodiments. Obviously, modifications and alterations will occur to others upon reading and understanding the proceeding detailed description. It is intended that the invention be construed as including all such modifications and alterations insofar as they come within the scope of the appended claims or the equivalents thereof.

The invention claimed is:

1. A temperature measurement probe for use in a magnetic resonance environment comprising:
   an elongated substrate;
   a plurality of resistive electrically conductive traces printed on the substrate;
   at least one thermistor disposed on the substrate and electrically connected with at least one of the traces, the thermistor configured to be placed in thermal communication with a patient in the magnetic resonance environment;
   at least one reference element connected with one of the resistive traces, wherein the at least one reference element includes a thermistor which is thermally isolated from the patient or a resistor; and
   a processor and control circuit electrically connected with the traces, the processor and control circuit being configured to subtractively combine a temperature signal with MR related noise and an MR related noise signal from the reference element.

2. The temperature measurement probe according to claim 1, wherein the traces are screen printed with a resistive, conductive ink.

3. The temperature measurement probe according to claim 1, wherein the traces are carbon-based.

4. The temperature measurement probe according to claim 1, wherein the traces include doped semiconductor material.

5. The temperature measurement probe according to claim 1, wherein the at least one highly resistive, electrically conductive trace resistance is on in the order of 26-33 k Ohms per meter.

6. The temperature measurement probe according to claim 1, wherein the traces are etched in a cross-hatch.

7. The temperature measurement probe according to claim 1, wherein the traces include an input trace which provides electric power to the thermistor and a return trace.

8. The temperature measurement probe according to claim 7, wherein the wherein the input and return traces are disposed on opposite faces of the substrate.

9. The temperature measurement probe according to claim 7, wherein the input and return traces are disposed on a common face of the substrate.

10. The temperature measurement probe according to claim 1, further including:
a plurality of thermistors disposed on the plurality of printed traces;
tear lines in the elongated substrate such that the printed traces are separable to accommodate positioning the plurality of thermistors for multi-site sensing on various patient body shapes.

11. The temperature measurement probe according to claim 1, further including:
a sterilisable protective jacket.

12. The temperature measurement probe according the claim 1, further including:
connection pads formed on the traces configured for electrical connection with the thermistor.

13. A magnetic resonance system, comprising:
a magnetic resonance scanner; and
the temperature measurement probe according to claim 1, wherein the thermistor and at least a portion of the substrate and the at least one trace is disposed in an examination region of the magnetic resonance scanner.

14. A method for monitoring temperature in a magnetic resonance environment comprising:
printing a plurality of resistive, electrically conductive traces on an elongated substrate;
electrically connect at least one patient temperature measuring thermistor to at least one of the traces;
connecting a reference element for sensing a common mode signal for subtraction from a signal from the patient temperature measuring thermistor to one of the traces, wherein the signal on trace from thermistor includes noise and temperature information, and the signal on trace from reference element includes the noise;
applying the thermistor and the reference element to the patient;
processing the signals from the thermistor and the reference element to correct the thermistor signal from the noise; and
convert corrected thermistor signal to a temperature value.

15. The method according to claim 14, further including:
conveying the temperature value to a monitor and displaying the temperature value on the monitor.

* * * * *